United States Patent
Thomas

(10) Patent No.: US 7,427,626 B2
(45) Date of Patent: Sep. 23, 2008

(54) 2-ANILINO-4-(IMIDAZOL-5-YL)-PYRIMIDINE DERIVATIVES AND THEIR USE AS CDK (CDK2) INHIBITORS

(75) Inventor: Andrew Peter Thomas, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 7 days.

(21) Appl. No.: 10/556,561

(22) PCT Filed: May 12, 2004

(86) PCT No.: PCT/GB2004/002025

§ 371 (c)(1), (2), (4) Date: Nov. 14, 2005

(87) PCT Pub. No.: WO2004/101549

PCT Pub. Date: Nov. 25, 2004

(65) Prior Publication Data

US 2007/0037839 A1    Feb. 15, 2007

(30) Foreign Application Priority Data

May 16, 2003 (GB) ................... 0311276.0

(51) Int. Cl.
C07D 403/04 (2006.01)
C07D 403/14 (2006.01)
A61K 31/4178 (2006.01)
A61K 31/506 (2006.01)
A61P 19/02 (2006.01)
A61P 35/00 (2006.01)

(52) U.S. Cl. ............... 514/275; 514/235.8; 514/255.05; 544/331; 544/122

(58) Field of Classification Search ................ 544/331, 544/122; 514/235.8, 255.05, 275
See application file for complete search history.

(56) References Cited

U.S. PATENT DOCUMENTS

| | | | |
|---|---|---|---|
| 4,983,608 A | 1/1991 | Effland et al. | |
| 5,516,775 A | 5/1996 | Zimmermann et al. | |
| 5,521,184 A | 5/1996 | Zimmermann | |
| 5,610,303 A | 3/1997 | Kimura et al. | |
| 5,739,143 A | 4/1998 | Adams et al. | |
| 5,859,041 A | 1/1999 | Liverton et al. | |
| 6,835,726 B2 | 12/2004 | Cushing et al. | |
| 6,969,714 B2 * | 11/2005 | Breault et al. ............ | 514/235.8 |
| 2003/0144303 A1 | 7/2003 | Hawley et al. | |
| 2003/0191307 A1 | 10/2003 | Blumenkopf et al. | |
| 2006/0079543 A1 | 4/2006 | Sum et al. | |

FOREIGN PATENT DOCUMENTS

| | | |
|---|---|---|
| CA | 2231765 | 9/1998 |
| EP | 0135472 | 1/1989 |
| EP | 0363002 | 6/1994 |
| EP | 0379806 | 4/1996 |
| EP | 1056742 | 7/2003 |
| EP | 0945443 | 8/2003 |
| HU | 220630 | 3/2002 |
| WO | WO 91/18887 | 12/1991 |
| WO | WO 92/20642 | 11/1992 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/15952 | 6/1995 |
| WO | WO 96/05177 | 2/1996 |
| WO | WO 96/28427 | 9/1996 |
| WO | WO 96/40143 | 12/1996 |
| WO | WO 97/19065 | 5/1997 |
| WO | WO 97/35856 | 10/1997 |
| WO | WO 97/40017 | 10/1997 |
| WO | WO 97/44326 | 11/1997 |
| WO | WO 97/47618 | 12/1997 |
| WO | WO 98/11095 | 3/1998 |
| WO | WO 98/16230 | 4/1998 |
| WO | WO 98/18782 | 5/1998 |
| WO | WO 98/25619 | 6/1998 |
| WO | WO 98/33798 | 8/1998 |
| WO | WO 98/41512 | 9/1998 |
| WO | WO 98/54093 | 12/1998 |
| WO | WO 98/56788 | 12/1998 |
| WO | WO 99/01136 | 1/1999 |
| WO | WO 99/18096 | 4/1999 |
| WO | WO 99/18942 | 4/1999 |
| WO | WO 99/31073 | 6/1999 |

(Continued)

OTHER PUBLICATIONS

Wolft Manfred E. "Burger's Medicinal Chemistry, 5ed, Part 1", John Wiley & Sons, 1995, pp. 975-977.*

(Continued)

*Primary Examiner*—Venkataraman Balasubram
(74) *Attorney, Agent, or Firm*—Morgan, Lewis & Bockius LLP

(57) ABSTRACT

Compounds of the formula (I), and pharmaceutically acceptable salts and in vivo hydrolysable esters thereof are described. Also described are processes for their preparation and their use as medicaments, particularly medicaments for producing a cell cycle inhibitory (anti cell proliferation) effect in a warm blooded animal, such as man.

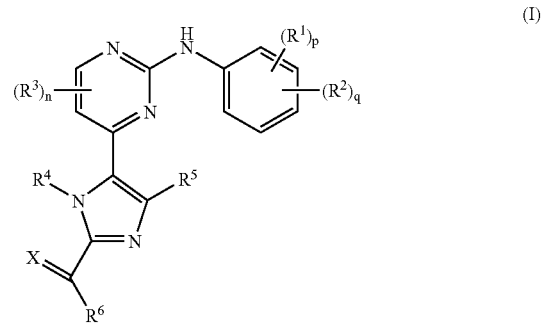

14 Claims, No Drawings

FOREIGN PATENT DOCUMENTS

| | | |
|---|---|---|
| WO | WO 99/32121 | 7/1999 |
| WO | WO 99/41253 | 8/1999 |
| WO | WO 99/50250 | 10/1999 |
| WO | WO 99/50251 | 10/1999 |
| WO | WO 00/12485 | 3/2000 |
| WO | WO 00/12486 | 3/2000 |
| WO | WO 00/17202 | 3/2000 |
| WO | WO 00/17203 | 3/2000 |
| WO | WO 00/21926 | 4/2000 |
| WO | WO 00/25780 | 5/2000 |
| WO | WO 00/26209 | 5/2000 |
| WO | WO 00/39101 | 7/2000 |
| WO | WO 00/44750 | 8/2000 |
| WO | WO 00/49018 | 8/2000 |
| WO | WO 00/53595 | 9/2000 |
| WO | WO 00/55161 | 9/2000 |
| WO | WO 00/59892 | 10/2000 |
| WO | WO 00/78731 | 12/2000 |
| WO | WO 01/14375 | 3/2001 |
| WO | WO 0129009 | 4/2001 |
| WO | WO 01/30778 | 5/2001 |
| WO | WO 01/37835 | 5/2001 |
| WO | WO 01/47897 | 7/2001 |
| WO | WO 01/47921 | 7/2001 |
| WO | WO 01/60816 | 8/2001 |
| WO | WO 01/64653 | 9/2001 |
| WO | WO 01/64654 | 9/2001 |
| WO | WO 01/64655 | 9/2001 |
| WO | WO 01/64656 | 9/2001 |
| WO | WO 01/72717 | 10/2001 |
| WO | WO 02/04429 | 1/2002 |
| WO | WO 02/20512 A1 | 3/2002 |
| WO | WO 02/46170 | 6/2002 |
| WO | WO 02/46171 | 6/2002 |
| WO | WO 02/065979 | 8/2002 |
| WO | WO 02/066480 | 8/2002 |
| WO | WO 02/066481 | 8/2002 |
| WO | WO 02/092573 | 11/2002 |
| WO | WO 02/096887 | 12/2002 |
| WO | WO 02/096888 | 12/2002 |
| WO | WO 03/007955 | 1/2003 |
| WO | WO 03/011837 | 2/2003 |
| WO | WO 03/029249 | 4/2003 |
| WO | WO 03/031446 | 4/2003 |
| WO | WO 03/037891 | 5/2003 |
| WO | WO 03/076433 | 9/2003 |
| WO | WO 03/076434 | 9/2003 |
| WO | WO 03/076435 | 9/2003 |
| WO | WO 03/076436 | 9/2003 |
| WO | WO 03/076494 A1 | 9/2003 |
| WO | WO 2004/005283 | 1/2004 |
| WO | WO 2004/043467 | 5/2004 |
| WO | WO 2004/043953 | 5/2004 |
| WO | WO 2004/087698 | 10/2004 |
| WO | WO 2004/087699 | 10/2004 |
| WO | WO 2004/101564 | 11/2004 |
| WO | WO 2005/012298 | 2/2005 |
| WO | WO 2005/037800 | 4/2005 |
| WO | WO 2005/075461 | 8/2005 |
| WO | WO 2005/075468 | 8/2005 |
| WO | WO 2005/113550 | 12/2005 |
| WO | WO 2005/116025 | 12/2005 |
| WO | WO 2006/034872 | 4/2006 |
| WO | WO 2006/044509 | 4/2006 |
| WO | WO 2006/050076 | 5/2006 |
| WO | WO 2006/064251 | 6/2006 |
| WO | WO 2006/075152 | 7/2006 |
| WO | WO 2006/095159 | 9/2006 |
| WO | WO 2007/015064 | 2/2007 |
| WO | WO 2007/036732 | 4/2007 |
| WO | WO 2007/040440 | 4/2007 |
| WO | WO 2007/138268 | 12/2007 |
| WO | WO 2007/138277 | 12/2007 |
| WO | WO 2007/148070 | 12/2007 |

OTHER PUBLICATIONS

Banker, G.S. et al, "Modern Pharmaceutics, 3ed.", Marcel Dekker, New York. 1996, pp. 451 and 596.*

Fischer Cell Cycle 3:6, 742-746, 2004.*

Malumbres et al., Trends in Biochemical Sciences, 30(11), 630-641, 2005.*

Lolli et al., Cell Cycle 4 :4, 572-577, 2005.*

Sherr et al., Genes & Development 18, 2699-2711, 2004.*

Cecil Textbook of Medicine, edited by Bennet, J.C., and Plum F., 20th edition,vol. 1, 1004-1010, 1996.*

Blain, S. et al. "Differential interaction of the cyclin-dependent kinase (Cdk) inhibitor p27$^{kip1}$ with cyclin A-Cdk2 and cyclin D2-Cdk4" The Journal of Biological Chemistry, 1997, vol. 272, No. 41, pp. 25863-25872.

Boschelli, D. et al. "Synthesis and tyrosine kinase inhibitory activity of a series of 2-amino-8H-pyrido[2,3-d]pyrimidines: identification of potent, selective platelet-derived growth factor receptor tyrosine kinase inhibitors" J. Med. Chem., 1998, vol. 41, pp. 4365-4377.

Deady L. et al. "Reactions of some quinazoline compounds with ethoxymethylenemalonic acid derivatives" J. Heterocyclic Chem., 1989, vol. 26, pp. 161-168.

El-Kerdawy, M. et al. "2,4-Bis(substituted)-5-nitropyrimidines of expected diuretic action" Egypt J. Chem., 1986, 29, vol. 2, No. 2, pp. 247-251.

Fiziol Akt Veshchestva, 1975, 7, pp. 68-72.

Ghosh, D. et al. "2,4-Bis(arylamino)-5-methylpyrimidines as antimicrobial agents" J. Med. Chem., 1967, vol. 10, pp. 974-975.

Ghosh, D., "2,4-Bis(arylamino)-6-methyl pyrimidines as antimicrobial agents" Chemical Abstracts, 1981, vol. 95, No. 11, Columbus, Ohio, US; Abstract No. 97712f; pp. 648; XP002109184 abstract & J. Indian Chem. Soc., 1981, vol. 58, No. 5, pp. 512-513, India.

Schmidt, H. et al. "A convenient synthesis of 2-substituted 4-amino-5-pyrimidinecarbonitriles" J. Heterocyclic Chem., 1987, vol. 24, pp. 1305-1307.

Simone, J. "Oncology: introduction" Bennett, J. Textbook of Medicine, 20th Edition, vol. 1, 1996, pp. 1004-1010.

Volin, M. et al. "Cell cycle implications in the pathogenesis of rheumatoid arthritis" Frontiers in Bioscience, 2000, 5, d594-601.

Zimmermann, J. et al. "Phenylamino-pyrimidine (PAP) derivatives: a new class of potent and selective inhibitors of protein kinase C (PKC)" Arch. Pharm. Pharm. Med. Chem. 1996, 329 (7), pp. 371-376.

Fiziol Akt Veshchestva 7:68-72 (1975) (Translantion enclosed).

* cited by examiner

2-ANILINO-4-(IMIDAZOL-5-YL)-PYRIMIDINE DERIVATIVES AND THEIR USE AS CDK (CDK2) INHIBITORS

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity and are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

The cell cycle is fundamental to the survival, regulation and proliferation of cells and is highly regulated to ensure that each step progresses in a timely and orderly manner. The progression of cells through the cell cycle arises from the sequential activation and de-activation of several members of the cyclin-dependent kinase (CDK) family. The activation of CDKs is dependent on their interaction with a family of intracellular proteins called cyclins. Cyclins bind to CDKs and this association is essential for CDK (such as CDK1, CDK2, CDK4 and/or CDK6) activity within the cell. Different cyclins are expressed and degraded at different points in the cell cycle to ensure that activation and inactivation of CDKs occurs in the correct order for progression through the cell cycle.

Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK1, CDK2 and/or CDK4 (which operate at the G2/M, G1-S-G2/M and G1-S phase respectively) should be of value as a selective inhibitor of cell proliferation, such as growth of mammalian cancer cells.

WO/01/14375, WO 01/72717, WO 02/04429, WO 02/20512, WO 02/66481, WO 02/096887, WO 03/076435, WO 03/076436, WO 03/076434 and WO 03/076433 describe certain pyrimidine derivatives that inhibit the effect of cell cycle kinases. The present invention is based on the discovery that an additional novel group of pyrimidine derivatives surprisingly inhibit the effects of cell cycle kinases showing selectivity for CDK1, CDK2 and/or CDK4, and thus possess anti-cell-proliferation properties. The compounds of the present invention are not specifically disclosed in any of the above applications. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

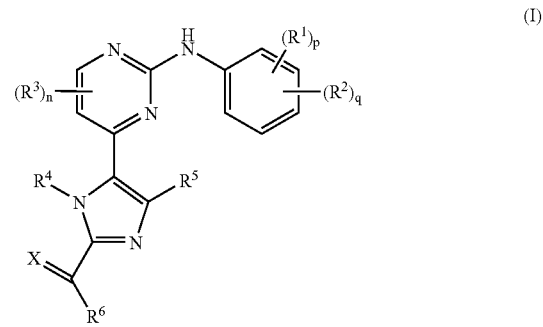

wherein:

$R^1$ is halo, nitro, cyano, hydroxy, amino, carboxy, carbamoyl, mercapto, $C_{1-6}$alkyl, $C_{1-6}$alkoxy, $C_{2-6}$alkenyl or $C_{2-6}$alkynyl;

p is 0-4; wherein the values of $R^1$ may be the same or different;

$R^2$ is sulphamoyl or a group $R^1$-$R^b$-;

q is 0-2; wherein the values of $R^2$ maybe the same or different; and wherein p+q=0-5;

$R^3$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-3}$alkyl)$_2$amino, $C_{1-3}$alkanoylamino, N-($C_{1-3}$alkyl)carbamoyl, N,N-($C_{1-3}$alkyl)$_2$carbamoyl, $C_{1-3}$aklylS(O)$_a$ wherein a is 0 to 2, N-($C_{1-3}$alkyl)sulphamoyl or N,N-($C_{1-3}$alkyl)$_2$sulphamoyl; wherein $R^3$ may be optionally substituted on carbon by one or more $R^c$;

n is 0 to 2, wherein the values of $R^3$ may be the same or different;

$R^4$ is hydrogen, $C_{1-6}$alkyl, $C_{2-6}$alkenyl, $C_{2-6}$alkynyl, $C_{3-8}$cycloalkyl, phenyl or a carbon-linked heterocyclic group; wherein $R^4$ may be optionally substituted on carbon by one or more $R^d$; and wherein if said heterocyclic group contains an —NH— moiety that nitrogen may be optionally substituted by a group selected from $R^n$;

$R^5$ is selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_6$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, $C_{3-8}$cycloalkyl or a 4-7 membered saturated heterocyclic group; wherein $R^5$ and $R^6$ independently of each other may be optionally substituted on carbon by one or more $R^e$; and wherein if said 4-7 membered saturated heterocyclic group contains an —NH— moiety that nitrogen may be optionally substituted by a group selected from $R^f$;

X is =O or =N—OR$^7$ (wherein "=" indicates the double bond depicted in formula (I);

$R^6$ and $R^7$ are independently selected from hydrogen, $C_{1-6}$alkyl, $C_{3-8}$cycloalkyl, phenyl or a heterocyclic group; wherein $R^6$ and $R^7$ may be independently optionally substituted on carbon by one or more $R^q$; and wherein if said heterocyclic group contains an —NH— moiety that nitrogen may be optionally substituted by a group selected from $R^r$;

$R^a$ is selected from $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, a heterocyclic group, phenyl$C_{1-6}$alkyl or (heterocyclic group)$C_{1-6}$alkyl; wherein $R^a$ may be optionally substituted on carbon by one or more $R^g$; and wherein if said heterocyclic group contains an —NH— moiety that nitrogen may be optionally substituted by a group selected from $R^h$;

$R^b$ is —C(O)—, —N($R^m$)C(O)—, —C(O)N($R^m$)—, —S(O)$_r$—, —OC(O)N($R^m$)SO$_2$—, —SO$_2$N($R^m$)— or —N($R^m$)SO$_2$—; wherein $R^m$ is hydrogen or $C_{1-6}$alkyl optionally substituted by one or more $R^j$ and r is 1-2;

$R^d$, $R^g$, $R^l$ and $R^q$ are independently selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkoxy$C_{1-6}$alkoxy, $C_{1-6}$alkoxy$C_{1-6}$alkoxy$C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alklylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, $C_{1-6}$alkylsulphonylamino, $C_{3-8}$cycloalkyl, phenyl, heterocyclic group, phenyl$C_{1-6}$alkyl-$R^o$—, (heterocyclic group)$C_{1-6}$alkyl-$R^o$—, phenyl-$R^o$— or (heterocyclic group)-$R^o$—; wherein $R^d$, $R^g$, $R^l$ and $R^q$ independently of each other may be optionally substituted on carbon by one or more $R^j$; and wherein if said heterocyclic group contains an —NH— moiety that nitrogen may be optionally substituted by a group selected from $R^k$;

$R^o$ is —O—, —N($R^p$)—, —C(O)—, —N($R^p$)C(O)—, —C(O)N($R^p$)—, —S(O)$_s$—, —SO$_2$N($R^p$)— or —N($R^p$)SO$_2$—; wherein $R^p$ is hydrogen or $C_{1-6}$alkyl and s is 0-2;

$R^f$, $R^h$, $R^k$, $R^n$ and $R^r$ are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl; wherein $R^f$, $R^h$, $R^k$, $R^n$ and $R^r$ independently of each other may be optionally substituted on carbon by on or more $R^i$; and $R^c$, $R^e$, $R^l$ and $R^j$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylarnino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; or a pharmaceutically acceptable salt or an in vivo hydrolysable ester thereof.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" includes phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —CH$_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and or the S-oxides. Examples and suitable values of the term "heterocyclic group" are morpholino, piperidyl, pyridyl pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Preferably a "heterocyclic group" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —CH$_2$— group can optionally be replaced by a —C(O)— and a ring sulphur atom may be optionally oxidised to form the S-oxides. More preferably a "heterocyclic group" is tetrahydrofuryl, pyridyl, pyrrolidinonyl, morpholino, imidazolyl, piperidinyl or pyrrolidinyl. Particularly a "heterocyclic group" is tetrahydrofuryl or morpholino. In another aspect of the invention, particularly a "heterocyclic group" is tetrahydrofuran-2-yl, 2-oxopyrrolidin-1-yl, furan-2-yl, oxazolyl, morpholino, piperidinyl, thiazolyl, pyrazinyl, isoxazolyl, tetrahydropyran, pyridyl, isoxazolyl, isothiazolyl, 1,2,5-thiadiazolyl, phthalimido.

A "4-7 membered saturated heterocyclic group" is a saturated monocyclic ring containing 4-7 atoms of which at least one atom is chosen from nitrogen, sulphur or oxygen, which may, unless otherwise specified, be carbon or nitrogen linked, wherein a —CH$_2$— group can optionally be replaced by a —C(O)— and a sulphur atom may be optionally oxidised to form the S-oxides. Examples and suitable values of the term "heterocyclic group" are morpholino, piperidyl, 1,4-dioxanyl, 1,3-dioxolanyl, 1,2-oxathiolanyl, imidazolidinyl, pyrazolidinyl, piperazinyl, thiazolidinyl, pyrrolidinyl, thiomorpholino, homopiperazinyl and tetrahydropyranyl.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylS(O)$_r$ wherein r is 1 to 2" include methylsulphinyl, ethylsulphinyl, mesyl and ethylsulphonyl. Examples of "$C_{1-6}$alkanoyl" include $C_{1-4}$alkanoyl, propionyl and acetyl. Examples of "N-$C_{1-6}$alkylamino" include methylamino and ethylamino. Examples of "N,N-($C_{1-6}$alkyl)$_2$amino" include di-N-methylamino, di-(N-ethyl)amino and N-ethyl-N-methylamino. Examples of "$C_{2-6}$alkenyl" are vinyl, allyl and 1-propenyl. Examples of "$C_{2-6}$alkynyl" are ethynyl, 1-propynyl and 2-propynyl. Examples of "N-($C_{1-6}$alkyl)sulphamoyl" are N-(methyl)sulphamoyl and N-(ethyl)sulphamoyl. Examples of "N-($C_{1-6}$alkyl)$_2$sulphamoyl" are N,N-(dimethyl)sulphamoyl and N-(methyl)-N-(ethyl)sulphamoyl.

Examples of "N-($C_{1-6}$alkyl)carbamoyl" are N-($C_{1-4}$alkyl)carbamoyl, methylaminocarbonyl and ethylaminocarbonyl. Examples of "N,N-($C_{1-6}$alkyl)$_2$carbamoyl" are N,N-($C_{1-4}$alkyl)$_2$carbamoyl, dimethylaminocarbonyl and methylethylaminocarbonyl. Examples of "$C_{3-8}$cycloalkyl" are cyclopropyl, cyclobutyl, cyclopropyl and cyclohexyl. Examples of "(heterocyclic group)$C_{1-6}$alkyl" include pyridylmethyl, 3-morpholinopropyl and 2-pyrimid-2-ylethyl. Examples of "$C_{3-8}$cycloalkyl$C_{1-6}$alkyl" are cyclopropylethyl, cyclobutylmethyl, 2-cyclopropylpropyl and cyclohexylethyl.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4- position of the benzoyl ring.

Some compounds of the formula (I) may have chiral centres and/or geometric isomeric centres (E- and Z- isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity. In particular the skilled reader will appreciate that when $R^4$ is hydrogen, the imidazole ring as drawn in formula (I) may tautomerise.

It is also to be understood that certain compounds of the formula (I) can exist in solvated as well as unsolvated forms such as, for example, hydrated forms. It is to be understood that the invention encompasses all such solvated forms which possess CDK inhibitory activity.

Preferred values of $R^1$, $R^2$, $R^3$, $R^4$, $R^5$, $R^6$, n, p and q are as follows. Such values may be used where appropriate with any of the definitions, claims or embodiments defined hereinbefore or hereinafter.

$R^1$ is halo.

$R^1$ is fluoro or chloro.

p is 0-2; wherein the values of $R^1$ may be the same or different.

p is 0 or 1.

p is 2; wherein the values of $R^1$ may be the same or different.

p is 1.

p is 0.

$R^2$ is a group $R^a$-$R^b$-; wherein $R^a$ is selected from $C^{1-6}$alkyl; wherein $R^a$ may be optionally substituted on carbon by one or more $R^g$; $R^b$ is —N($R^m$)SO$_2$—; wherein $R^m$ is hydrogen; and $R^g$ is $C_{1-6}$alkoxy.

$R^2$ is N-(2-methoxyethyl)sulphamoyl.

q is 0 or 1.

q is 0.

q is 1.

$R^3$ is halo.

$R^3$ is fluoro, chloro or bromo.

$R^3$ is chloro or bromo.

n is 0.

$R^4$ is $C_{1-6}$alkyl.

$R^4$ is isopropyl.

$R^5$ is hydrogen.

X is =O.

X is =N—O$R^7$.

$R^6$ is selected from hydrogen, $C_{1-6}$alkyl, phenyl or a heterocyclic group; wherein $R^6$ may be optionally substituted on carbon by one or more $R^q$; and $R^q$ is selected from phenyl.

$R^6$ is selected from hydrogen, phenyl, pyridyl, thienyl or phenethyl.

$R^6$ is selected from hydrogen, phenyl, pyrid4-yl, thien-2-yl or phenethyl.

$R^7$ is selected from hydrogen or $C_{1-6}$alkyl; wherein $R^7$ may be optionally substituted on carbon by one or more $R^q$; wherein $R^q$ is phenyl.

$R^7$ is selected from hydrogen, t-butyl or benzyl.

Therefore, in a further aspect of the invention, there is provided a compound of formula (I) (as depicted above) wherein:

p is 0;

$R^2$ is a group $R^a$-$R^b$-; wherein $R^a$ is selected from $C_{1-6}$alkyl; wherein $R^a$ may be optionally substituted on carbon by one or more $R^g$; $R^b$ is —N($R^m$)SO$_2$—; wherein $R^m$ is hydrogen; and $R^g$ is $C_{1-6}$alkoxy;

q is 0 or 1;

n is 0;

$R^4$ is $C_{1-6}$alkyl;

$R^5$ is hydrogen;

X is =O or =N—O$R^7$;

$R^6$ is selected from hydrogen, $C_{1-6}$alkyl, phenyl or a heterocyclic group; wherein $R^6$ may be optionally substituted on carbon by one or more $R^q$; and $R^q$ is selected from phenyl; and $R^7$ is selected from hydrogen or $C_{1-6}$alkyl; wherein $R^7$ may be optionally substituted on carbon by one or more $R^q$; wherein $R^q$ is phenyl; or a pharmaceutically acceptable salt or an in vivo hydrolysable ester thereof.

Therefore, in a further aspect of the invention, there is provided a compound of formula (I) (as depicted above) wherein:

p is 0;
$R^2$ is N-(2-methoxyethyl)sulphamoyl;
q is 0 or 1;
n is 0;
$R^4$ is isopropyl;
$R^5$ is hydrogen;
X is =O or =N—$OR^7$;
$R^6$ is selected from hydrogen, phenyl, pyrid-4-yl, thien-2-yl or phenethyl; and
$R^7$ is selected from hydrogen, t-butyl or benzyl; or a pharmaceutically acceptable salt or an in vivo hydrolysable ester thereof.

In another aspect of the invention, preferred compounds of the invention are any one of the Examples or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, $R^4$, $R^5$, $R^6$, n, p and q are, unless otherwise specified, as defined in formula (I)) comprises of:

Process a) reaction of a pyrimidine of formula (II):

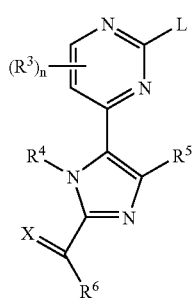

(II)

wherein L is a displaceable group; with an aniline of formula (III):

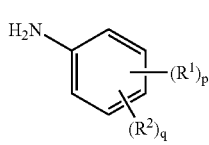

(III)

or

Process b) reacting a compound of formula (IV):

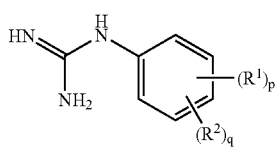

(IV)

with a compound of formula (V):

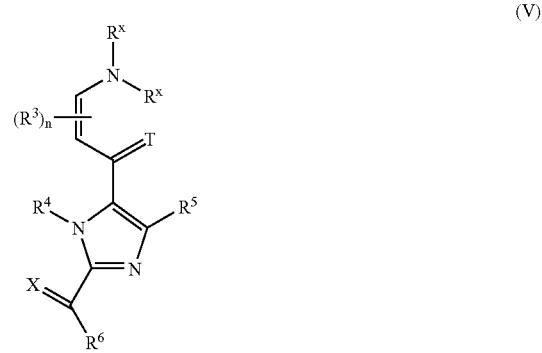

(V)

wherein T is O or S; $R^x$ may be the same or different and is selected from $C_{1-6}$alkyl;

Process c) for compounds of formula (I) where $R^2$ is sulphamoyl or a group $R^a$-$R^b$- and $R^b$ is —$NHSO_2$; reacting a pyrimidine of formula (VI):

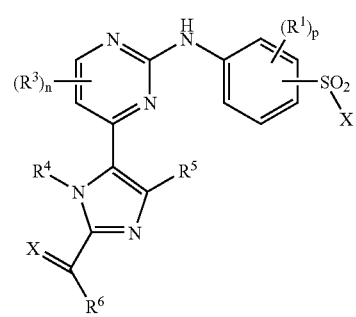

(VI)

wherein X is a displaceable group; with ammonia or an amine of formula (VII):

$$R^a—NH_2 \quad \text{(VII)}$$

Process d) for compounds of formula (I); reacting a pyrimidine of formula (VIII)

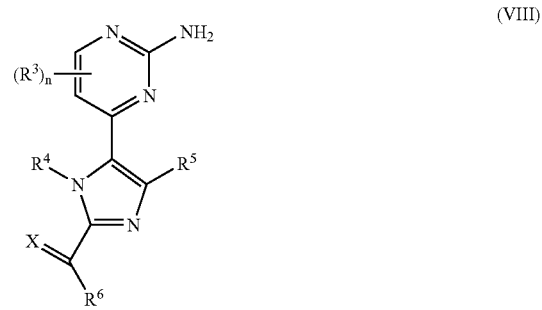

(VIII)

with a compound of formula (IX):

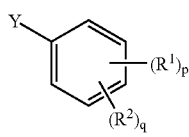
(IX)

where Y is a displaceable group;

Process e) for compounds of formula (I) wherein X is =N—OR$^7$ reacting a compound of formula (I) wherein X is =O with a compound of formula (X):

(X)

Process f) for compounds of formula (I) wherein X is =O reacting a compound of formula (XI):

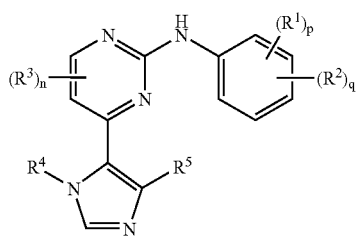
(XI)

with a compound of formula (XII):

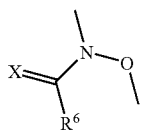
(XII)

and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4sulphonyloxy group.

X is a displaceable group, suitable values for X are for example, a fluoro or chloro group. Preferably X is fluoro.

Y is a displaceable group, suitable values for Y are for example, a halogeno or sulphonyloxy group, for example a bromo, iodo or trifluoromethanesulphonyloxy group. Preferably Y is iodo.

Specific reaction conditions for the above reactions are as follows.

Process a) Pyrimidines of formula (II) and anilines of formula (III) may be reacted together:
i) in the presence of a suitable solvent for example a ketone such as acetone or an alcohol such as ethanol or butanol or an aromatic hydrocarbon such as toluene or N-methyl pyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or ii) under standard Buchwald conditions (for example see *J. Am. Chem. Soc.*, 118, 7215; *J Am. Chem. Soc.*, 119, 8451; *J Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) where L is chloro may be prepared according to Scheme 1:

Scheme 1

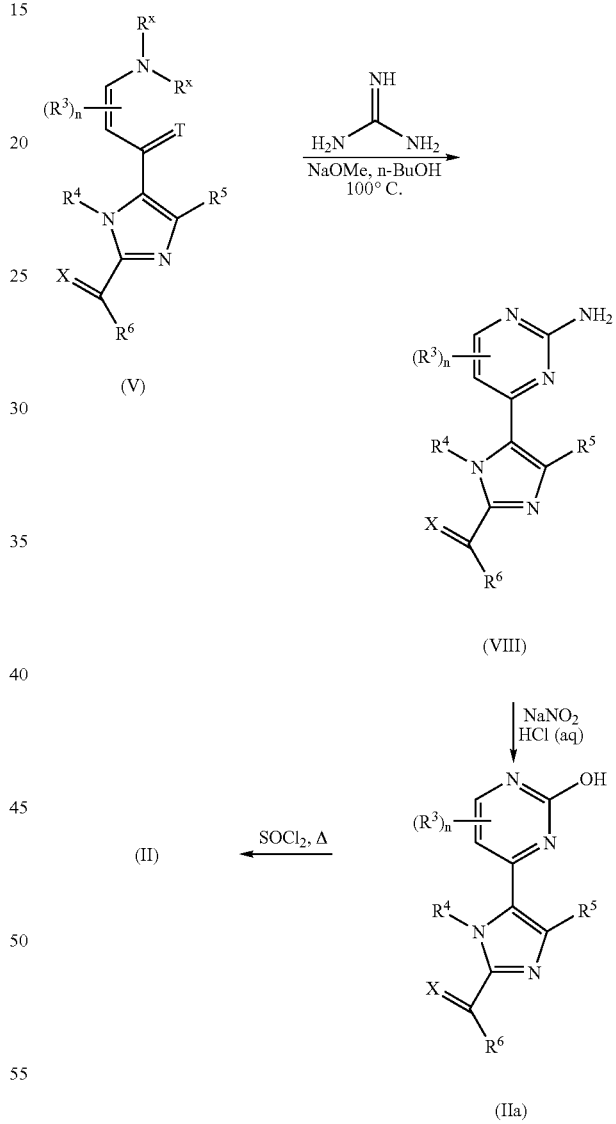

Anilines of formula (III) are commercially available compounds, or they are known in the literature, or they are prepared by standard processes known in the art.

Process b) Compounds of formula (IV) and compounds of formula (V) are reacted together in a suitable solvent such as N-methylpyrrolidinone or butanol at a temperature in the range of 100-200° C., preferably in the range of 150-170° C. The reaction is preferably conducted in the presence of a suitable base such as, for example, sodium hydride, sodium methoxide or potassium carbonate.

Compounds of formula (V) may be prepared according to Scheme 2:

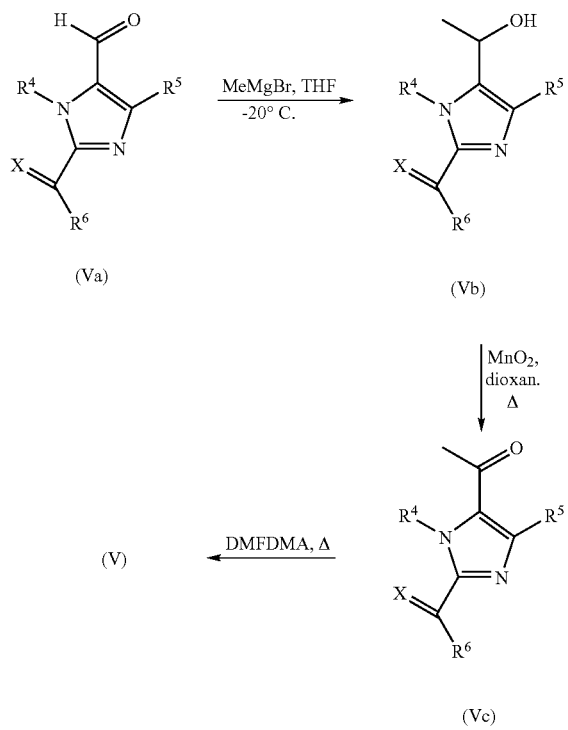

Compounds of formula (IV) and (Va) are commercially available compounds, or they are known in the literature, or they are prepared by standard processes known in the art.

Process c) Compounds of formula (VI) and amines of formula (VII) may be reacted together in the presence of an inert solvent such as N-methylpyrrolidinone or pyridine, in the presence of a base for example an inorganic base such as caesium carbonate or in the presence of an organic base such as excess (VII) and at a temperature in the range of 25 to 80° C.

Compounds of formula (VI) (wherein X is chloro) may be prepared according to Scheme 3:

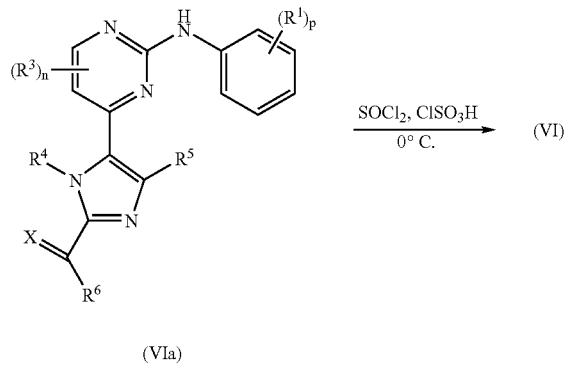

Compounds of formula (VIa) may be prepared according to Process a, Process b or Process d wherein q is 0.

Process d) Compounds of formula (VI) and amines of formula (IX) may be reacted together under standard Buchwald conditions as described in Process a.

The synthesis of compounds of formula (VI) is described in Scheme 1.

Compounds of formula (IX) are commercially available compounds, or they are known in the literature, or they are prepared by standard processes known in the art.

Amines of formula (VI) are commercially available compounds, or they are known in the literature, or they are prepared by standard processes known in the art.

Process e) Compounds of formula (I) wherein X is =O may be reacted with a compound of formula (X) in a solvent such as ethanol.

Compounds of formula (X) are commercially available compounds, or they are known in the literature, or they are prepared by standard processes known in the art.

Process f) Compounds of formula (XI) may be reacted with butyl lithium in an inert solvent such as THF at −70° C. to −80° C. and the resulting anion reacted with a compound of formula (XII) at a temperature of −80° C. to ambient temperature.

Compounds of formula (XI) may be prepared by the procedures described herein for preparation of compounds of formula (I) but wherein the C(=X)$R^6$ moiety is hydrogen.

Compounds of formula (XII) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifing group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anti-cancer activity which is believed to arise from the CDK inhibitory activity of the compound. These properties may be assessed, for example, using the procedure set out below:

Assay

The following abbreviations have been used:
HEPES is N-[2-Hydroxyethyl]piperazine-N'-[2-ethanesulfonic acid]
DTT is Dithiothreitol
PMSF is Phenylmethylsulphonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 µl of CDK2/Cyclin E partially-purified enzyme (amount dependent on enzyme activity) diluted in 25 µl incubation buffer was added to each well then 20 µl of GST-Rb/ATP/ATP33 mixture (containing 0.5 µg GST-Rb and 0.2 µM ATP and 0.14 µCi [γ-33-P]-Adenosine Triphosphate in incubation buffer), and the resulting mixture shaken gently, then incubated at room temperature for 60 minutes.

To each well was then added 150 µL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124 xg., for 5 minutes. The plates were read on a Topcount for 30 seconds per well.

The incubation buffer used to dilute the enzyme and substrate mixes contained 50 mM HEPES pH 7.5, 10 mM $MnCl_2$, 1 mM DTT, 100 µM Sodium vanadate, 100 µM NaF, 10 mM Sodium Glycerophosphate, BSA (1 mg/ml final).

Test Substrate

In this assay only part of the retinoblastoma protein (Science 1987 Mar. 13; 235(4794): 1394-1399; Lee W. H., Bookstein R., Hong F., Young L. J., Shew J. Y., Lee E. Y.) was used, fused to a GST tag. PCR of retinoblastoma gene encoding amino acids 379-928 (obtained from retinoblastoma plasmid ATCC pLRbRNL) was performed, and the sequence cloned into pGEx 2T fusion vector (Smith D. B. and Johnson, K. S. Gene 67, 31 (1988); which contained a tac promoter for inducible expression, internal lac $I^q$ gene for use in any *E. Coli* host, and a coding region for thrombin cleavage—obtained from Pharmacia Biotech) which was used to amplify amino acids 792-928. This sequence was again cloned into pGEx 2T.

The retinoblastoma 792-928 sequence so obtained was expressed in *E. Coli* (BL21 (DE3) pLysS cells) using standard inducible expression techniques, and purified as follows.

*E. coli* paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 µg/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792-927) were pooled and dialysed overnight against kinase buffer. The final product was analysed by Sodium Dodeca Sulfate (SDS) PAGE (Polyacrylamide gel) using 8-16% Tris-Glycine gels (Novex, San Diego, USA).

CDK2 and Cyclin E

The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number: V1392-20). CDK2 and cyclin E were then dually expressed [using a standard virus Baculogold co-infection technique] in the insect SF21 cell system (Spodoptera Frugiperda cells derived from ovarian tissue of the Fall Army Worm—commercially available).

Example Production of Cyclin E/CDK2

The following Example provides details of the production of Cyclin E/CDK2 in SF21 cells (in TC100+10% FBS(TCS)+ 0.2% Pluronic) having dual infection MOI 3 for each virus of Cyclin E & CDK2.

SF21 cells grown in a roller bottle culture to $2.33 \times 10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Litres of culture was harvested. The total cell count at harvest was 1.58×10E6 cells/ml. (99% viable). The cells were spun out at 2500 rpm, 30 mins., 4° C. in Heraeus Omnifuge 2.0 RS in 250 ml. lots.

The supernatant was discarded.

Partial Co-purification of Cdk2 and Cyclin E

Sf21 cells were resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Biosystems, Hertford, UK). Cdk2 and Cyclin E were coeluted at the beginning of a 0-1 M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK1 and CDK4 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 25 μM to 1 nM.

The following $IC_{50}$s were measured in the above assay.

| Example No | $IC_{50}$ |
|---|---|
| 6 | 65 nM |
| 8 | 4 nM |
| 9 | 64 nM |

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1-12). Thus, the following details are provided of measuring inhibition of cell growth:

Cells were plated in appropriate medium in a volume of 100 μl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% $CO_2$) for three days.

At the end of three days TCA was added to the plates to a final concentration of 16% (v/v). Plates were then incubated at 4° C. for 1 hour, the supernatant removed and the plates washed in tap water. After drying, 100 μl SRB dye (0.4% SRB in 1% acetic acid) was added for 30 minutes at 37° C. Excess SRB was removed and the plates washed in 1% acetic acid. The SRB bound to protein was solubilised in 10 mM Tris pH 7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5-5000 mg per square meter body area of the animal, i.e. approximately 0.1-100 mg/kg, and this normally provides a therapeutically-effective dose. A unit dose form such as a tablet or capsule will usually contain, for example 1-250 mg of active ingredient. Preferably a daily dose in the range of 1-50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2 and CDK4, especially CDK2, and M phase by inhibition of CDK1.

According to a further feature of the invention, there is provided a compound of the formula (I), or a pharmaceutically acceptable salt or in vivo hydrolysable ester thereof, as defined herein before in the manufacture of a medicament for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, particularly in the treatment of cancers.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2 and CDK4, especially CDK2, and M phase by inhibition of CDK1.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound of formula (I) or a pharmaceutically acceptable salt or in vivo hydrolysable ester thereof as defined herein before. Particularly, an inhibitory effect is produced by preventing entry into or progression through the S phase by inhibition of CDK2 and CDK4, especially CDK2, and M phase by inhibition of CDK1.

According to an additional feature of this aspect of the invention there is provided a method of treating cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal, such as man, in need of such treatment which comprises administering to said animal an effective amount of a compound of formula (I) or a pharmaceutically acceptable salt or in vivo hydrolysable ester thereof as defined herein before.

Particularly there is provided a method of treating cancer in a warm-blooded animal, such as man, in need of such treatment which comprises administering to said animal an effective amount of a compound of formula (I) or a pharmaceutically acceptable salt or in vivo hydrolysable ester thereof as defined herein before.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the production of a cell cycle inhibitory (anti-cell-proliferation) effect in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancers (solid tumours and leukaemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation, in a warm-blooded animal such as man.

In a further aspect of the invention there is provided a pharmaceutical composition which comprises a compound of the formula (I), or a pharmaceutically acceptable salt or in vivo hydrolysable ester thereof, as defined herein before in association with a pharmaceutically-acceptable diluent or carrier for use in the treatment of cancer in a warm-blooded animal such as man.

Preventing cells from entering DNA synthesis by inhibition of essential S-phase initiating activities such as CDK2 initiation may also be useful in protecting normal cells of the body from toxicity of cycle-specific pharmaceutical agents. Inhibition of CDK2 or 4 will prevent progression into the cell cycle in normal cells which could limit the toxicity of cycle-specific pharmaceutical agents which act in S-phase, G2 or mitosis. Such protection may result in the prevention of hair loss normally associated with these agents.

Therefore in a further aspect of the invention there is provided a compound of formula (I) as defined above or a pharmaceutically acceptable salt or in vivo hydrolysable ester thereof for use as a cell protective agent.

Therefore in a further aspect of the invention there is provided a compound of formula (I) as defined above or a pharmaceutically acceptable salt or in vivo hydrolysable ester thereof for use in preventing hair loss arising from the treatment of malignant conditions with pharmaceutical agents.

Examples of pharmaceutical agents for treating malignant conditions that are known to cause hair loss include alkylating agents such as ifosfamide and cyclophosphamide; antimetabolites such as methotrexate, 5-fluorouracil, gemcitabine and cytarabine; vinca alkaloids and analogues such as vincristine, vinbalstine, vindesine, vinorelbine; taxanes such as paclitaxel and docetaxel; topoisomerase I inhibitors such as irintotecan and topotecan; cytotoxic antibiotics such as doxorubicin, daunorubicin, mitoxantrone, actinomycin-D and mitomycin; and others such as etoposide and tretinoin.

In another aspect of the invention, the compound of formula (I), or a pharmaceutically acceptable salt or in vivo hydrolysable ester thereof, may be administered in association with a one or more of the above pharmaceutical agents. In this instance the compound of formula (I) may be administered by systemic or non systemic means. Particularly the compound of formula (I) my may administered by non-systemic means, for example topical administration.

Therefore in an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof.

In an additional feature of the invention, there is provided a method of preventing hair loss during treatment for one or more malignant conditions with pharmaceutical agents, in a warm-blooded animal, such as man, which comprises administering to said animal an effective amount of a compound of formula (I), or a pharmaceutically acceptable salt or in vivo hydrolysable ester thereof in simultaneous, sequential or separate administration with an effective amount of said pharmaceutical agent.

According to a further aspect of the invention there is provided a pharmaceutical composition for use in preventing hair loss arising from the treatment of malignant conditions with pharmaceutical agents which comprises a compound of formula (I), or a pharmaceutically acceptable salt or in vivo hydrolysable ester thereof, and said pharmaceutical agent, in association with a pharmaceutically acceptable diluent or carrier.

According to a further aspect of the present invention there is provided a kit comprising a compound of formula (I), or a pharmaceutically acceptable salt or in vivo hydrolysable ester thereof, and a pharmaceutical agent for treating malignant conditions that is known to cause hair loss.

According to a further aspect of the present invention there is provided a kit comprising:
a) a compound of formula (I), or a pharmaceutically acceptable salt or in vivo hydrolysable ester thereof, in a first unit dosage form;
b) a pharmaceutical agent for treating malignant conditions that is known to cause hair loss; in a second unit dosage form; and
c) container means for containing said first and second dosage forms.

According to another feature of the invention there is provided the use of a compound of the formula (I), or a pharmaceutically acceptable salt or in vivo hydrolysable ester thereof, in the manufacture of a medicament for the prevention of hair loss during treatment of malignant conditions with pharmaceutical agents.

According to a further aspect of the present invention there is provided a combination treatment for the prevention of hair loss comprising the administration of an effective amount of a compound of the formula (I), or a pharmaceutically acceptable salt or in vivo hydrolysable ester thereof, optionally together with a pharmaceutically acceptable diluent or carrier, with the simultaneous, sequential or separate administration of an effective amount of a pharmaceutical agent for treatment of malignant conditions to a warm-blooded animal, such as man.

As stated above the size of the dose required for the therapeutic or prophylactic treatment of a particular cell-proliferation disease will necessarily be varied depending on the host treated, the route of administration and the severity of the illness being treated. A unit dose in the range, for example, 1-100 mg/kg, preferably 1-50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non limiting examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(MH)^+$;

(xi) unless stated otherwise compounds containing an asymmetrically substituted carbon and/or sulphur atom have not been resolved;

(xii) where a synthesis is described as being analogous to that described in a previous example the amounts used are the millimolar ratio equivalents to those used in the previous example; and (xvi) the following abbreviations have been used:

| | |
|---|---|
| THF | tetrahydrofuran; |
| DMF | N,N-dimethylformamide; |
| DMFDMA | dimethylformamide dimethylacetal; |
| EtOAc | ethyl acetate; |
| MeOH | methanol; |
| EtOH | ethanol; |
| DCM | dichloromethane; and |
| DMSO | dimethylsulphoxide. |

Example 1

2-Anilino-4-[1-isopropyl-2-(hydroxyiminomethyl) imidazol-5-yl]pyrimidine

Pyridine (283 μl, 3.50 mmol) was added to a solution of 2-anilino-4-(2-formyl-1-isopropylimidazol-5-yl)pyrimidine (Example 10; 250 mg, 0.814 mmol) and hydroxylamine.hydrochloride (283 mg, 4.07 mmol) in EtOH (8 ml) and the reaction mixture heated at reflux for 1 hr. The mixture was allowed to cool, water (10 ml) was added and the EtOH was removed by evaporation. Further water (10 ml) was added to the aqueous residue and the precipitated solid was collected by filtration, washed with water and dried to give the title compound as a 9:1 mixture of E and Z isomers (142 mg, 54%) as a white solid. NMR: Major isomer: 1.47 (d, 6H), 5.70 (m, 1H), 6.95 (t, 1H), 7.10 (d, 1H), 7.31 (t, 2H), 7.60 (s,1 H) 7.69 (d, 2H), 8.25 (s, 1H), 8.50 (d, 1H), 9.50 (s, 1H), 11.70 (s, 1 H); Minor isomer: 1.47 (d,6H), 5.70 (m, 1H), 6.95 (t, 1H), 7.19 (d, 1H), 7.31 (t, 2H), 7.69 (d, 2H), 7.78 (s, 1H), 8.10 (s, 1H), 8.52 (d, 1H), 9.57 (s, 1H), 13.89 (s, 1 H); m/z 323.

Example 2

4-[1-Isopropyl-2-(hydroxyiminomethyl)imidazol-5-yl]-2-{4-[N-(2-methoxyethyl)sulphamoyl]anilino}pyrimidine The title compound was prepared by the procedure of Example 1 from 4-(2-formyl-1-isopropylimidazol-5-yl)-2{4-[N-(2-methoxyethyl)sulphamoyl]anilino}pyrimidine (Example 11). NMR: 1.50 (d, 6H), 2.86 (q, 2H), 3.15 (s, 3H), 3.27 (m, 4H), 5.64 (m, 1H), 7.21 (d, 1H), 7.48 (t, 1H), 7.60 (s, 1H), 7.70 (d, 2H), 7.89 (d, 2H), 8.22 (s, 1H), 8.58 (d, 1H), 9.95 (s, 1H), (11.73 (s, 1 H); m/z 460.

Example 3

2-Anilino-4-[1-isopropyl-2-(methoxyiminomethyl) imidazol-5-yl]pyrimidine

Methoxylamine hydrochloride (340 mg, 4.07 mmol) and pyridine (322 mg, 4.07 mmol) was added to a solution of 2-anilino-4-(2-formyl-1-isopropylimidazol-5-yl)pyrimidine (Example 10; 250 mg, 0.814 mmol) in EtOH (10 ml) and the mixture was stirred at ambient temperature for 18 hours. The volatiles were removed by evaporation and the residue triturated with water. The solid product was collected by filtration and dried at 50° C. under vacuum to give the title compound (248 mg, 91%) as a white crystalline solid. NMR (CDCl$_3$): 1.54 (d, 6H), 4.07 (s, 3H), 5.65-5.80 (sept, 1H), 6.95 (d, 1H), 7.15 (m, 2H), 7.34 (t, 2H), 7.50 (s 1H), 7.57 (d, 2H), 8.28 (s, 1H), 8.41 (d, 1 H); m/z 337.

Example 4

2-Anilino-4-[1-isopropyl-2-(t-butoxyiminomethyl) imidazol-5-yl]pyrimidine

The title compound was prepared by the procedure of Example 3 from 2-anilino4-(2-formyl-1-isopropylimidazol-5-yl)pyrimidine (Example 10). NMR (CDCl$_3$): 1.38 (s, 9H), 1.55-1.60 (m, 8H), 5.60-5.75 (sept, 1H), 6.92 (d, 1H), 7.04-7.10 (m, 2H), 7.34 (t, 2H), 7.48 (s, 1H), 7.54-7.60 (m, 2H), 8.24 (s, 1H), 8.41 (d, 1 H); m/z 379.

Example 5

2-Anilino-4-[1-isoipropyl-2-(benzyloxyiminomethl) imidazol-5-yl]pyrimidine

The title compound was prepared by the procedure of Example 3 from 2-anilino-4-(2-formyl-1-isopropylimidazol-5-yl)pyrimidine (Example 10). NMR (CDCl$_3$): 4.49 (d, 6H), 5.28 (s, 2H), 5.58-5.72 (sept, 1H), 6.90 (d, 1H), 7.06-7.14 (m, 2H), 7.30-7.46 (m, 7H), 7.50 (s, 1H), 7.56 (d, 2H), 8.35 (s, 1H), 8.40 (d, 1 H); m/z 413.

Example 6

2-Anilino4(2-benzoyl-1-isopropylimidazol-5-yl) pyrimidine n-Butyllithium (3.12 ml of 1.6 M solution in hexane, 5.0 mmol) was added to a stirred solution of 2-anilino-4-(2-formyl-1-isopropylimidazol-5-yl)pyrimidine (Example 10; 558 mg, 2.0 mmol) in anhydrous THF (20 ml) cooled to −70° C. The mixture was stirred for 30 minutes and then N-methoxy-N-methylbenzamide (660 mg, 4.0 mmol) was added and the reaction mixture was allowed to warm and stirred at ambient temperature for 18 hour. The reaction mixture was quenched with water (20 ml), and extracted with EtOAc (4×25 ml). The organic extracts were washed with brine (2×50 ml), dried and the volatiles removed by evaporation and the residue triturated with ether and the solid collected by filtration to give the title compound (303 mg, 43%) as a pale yellow crystalline solid. NMR (CDCl$_3$): 1.55-1.70 (m, 8H), 5.52-5.68 (sept, 1H), 6.99 (d, 1H), 7.09 (dt, 1H), 7.18 (br s, 1H), 7.30-7.40 (m, 2H), 7.45-7.54 (m, 2H), 7.55 (s, 1H), 7.56-7.62 (m, 3H), 8.09 (d, 2H), 8.49 (d, 1 H); m/z 384.

Example 7

2-Anilino-4-[2-(thien-2-ylcarbonyl)-1-isopropylimidazol-5-yl]pyrimidine

The title compound was prepared by the procedure of Example 6 from 2-anilino-4-(2-formyl-1-isopropylimidazol-5-yl)pyrimidine (Example 10) and N-methoxy-N-methyl 2-thiophenecarboxamide (Method 6). NMR (CDCl$_3$): 1.64 (d, 6H), 5.54-5.68 (sept, 1H), 6.98 (d, 1H), 7.10 (t, 1H), 7.15-7.20 (m, 2H), 7.30-7.40 (m, 2H), 7.54 (s, 1H ), 7.60 (d, 2H), 7.73 (d, 1H), 8.28-8.30 (m, 1H), 8.49 (d, 1H); m/z 390.

Example 8

2-Anilino-4-[2-(pyridin-4-ylcarbonyl)-1-isopropylimidazol-5-yl]pyrimidine

The title compound was prepared by the procedure of Example 6 from 2-anilino-4-(2-formyl-1 -isopropylimidazol-5-yl)pyrimidine (Example 10) and N-methoxy-N-methyl 4-pyridinecarboxamide (Method 7). NMR (CDCl$_3$): 1.55-1.75 (m, 10H), 5.56-5.72 (sept, 1H), 6.98 (d, 1H), 7.10 (t, 1H), 7.20 (br s, 1H), 7.30-7.40 (m, 2H), 7.55 (s, 1H) (7.60 (d, 2H), 7.90-7.94 (m, 2H), 8.51 (d, 1H), 8.78-8.82 (m, 2 H); m/z 385.

Example 9

2-Anilino-4-[2-(3-phenylpropionyl)-1-isopropylimidazol-5-yl]pyrimidine

The title compound was prepared by the procedure of Example 6 from 2-anilino4(2-formyl-1-isopropylimidazol-5 - yl)pyrimidine (Example 10) and N-methoxy-N-methyl 3-phenylpropionamide (Method 8). NMR (CDCl$_3$): 1.54 (d, 6H), 3.07 (t, 2H), 3.55 (t, 2H), 5.50-5.65 (sept, 1H), 6.93 (d, 1H), 7.05-7.23 (m, 3H), 7.24-7.48 (m, 7H), 7.6 (d, 2H), 8.48 (d, 1 H); m/z 412.

Example 10

2-Anilino-4-(2-formyl-1-isopropylimidazol-5-yl) pyrimidine n-Butyllithium (7.2 ml of 1.6 M solution in hexane, 11.2 mmol) was added to a solution of 4-(1-isopropylimidazol-5-yl)-2-anilinopyrimidine (Method 5; 1.25 g, 4.48 mmol) in anhydrous THF (50 ml) cooled to −70° C., and the reaction mixture was then stirred at −70° C. for 30 minutes. Anhydrous DMF (0.7 ml, 9.0 mmol) was added and the mixture was stirred for 18 hour at ambient temperature. The mixture was quenched with water (50 ml), and was extracted with EtOAc (4×75 ml). The organic extracts were combined, washed with brine (2×50 ml), dried and evaporated. The residue was purified by chromatography eluting with EtOAc/Hexane (1:1) to give the title compound (930 mg, 68%) as a pale yellow crystalline solid. NMR (CDCl$_3$): 1.6 (d, 6H), 5.60-5.75 (m, 1H), 6.98 (d, 1H), 7.12 (t, 1H) , 7.30-7.40 (m, 3H), 7.55-7.65 (m, 3H), 8.50(d, 1H), 9.90 (s, 1H); m/z 308.

Example 11

4-(2-Formyl-1-isopropylimidazol-5-yl)-2-{4-[N-(2-methoxyethyl)sulphamoyl]anilino}pyrimidine Chlorosulphonic acid (70 µl, 1.0 mmol) was added dropwise to solution of 2-anilino-4-(2-formyl-1-isopropylimidazol-5-yl)pyrimidine (Example 10; 75 mg, 0.24 mmol) in thionyl chloride (2 ml) cooled at 0° C. and the mixture was stirred at 0° C. for 10 minutes then heated at 90° C. for 90 minutes. The volatiles were removed by evaporation and the residue was dried under high vacuum (<2 mmHg) for 1 hour. The resulting solid was placed under nitrogen and a solution of 2-methoxyethylamine (100 µl, 0.5 mmol) and diethylmethylamine (0.5 ml, 7.5 mmol) in MeOH (1.5 ml) added. The mixture was stirred for 30 minutes and the volatiles were evaporated in vacuo. The residue was purified by chromatography eluting with DCM/MeOH (98:2) to give the title compound (26 mg, 24%) as glassy solid. NMR: 1.53 (d, 6H) 2.86 (q, 2H) 3.17 (s, 3H) 3.28 (t, 2H) 5.65 (m, H) 7.3 (t, 1H) 7.50 (t, 1H) 7.71 (d, 2H) 7.83 (s, 1H) 7.89 (d, 2H) 8.68 (d, 1H) 9.81 (s, 1H) 10.11 (s, 1H).

Preparation of Starting Materials

The starting materials for the Examples above are either commercially available or are readily prepared by standard methods from known materials. For example the following reactions are illustrations but not limitations of the preparation of some of the starting materials used in the above reactions.

Methods 1-3

The following compounds were synthesised by the procedure as described in JOC 1987, 2714-2716.

| Meth | Compound | NMR | m/z | SM |
|---|---|---|---|---|
| 1 | 4-(Isopropylamino)-5-methylisoxazole | (CDCl$_3$)1.12(d, 6H), 2.30(s, 3H), 3.21(1H, sept), 8.01(s, 1H) | 141 | |
| 2 | 5-Methyl-4-(N-isopropyl-formido)isoxazole | Used crude | | Meth 1 |
| 3 | 5-Acetyl-1-isopropylimidazole | 1.38(d, 6H), 2.48(s, 3H), 5.13(q, 2H), 7.86(s, 1H), 8.10(s, 1H) | 153 | Meth 2 |

Method 4

5-(3-Dimethylaminoprop-2-en-1-oyl)-1-isopropylimidazole

5-Acetyl-1-isopropylimidazole (Method 3; 15.3 g, 100 mmol) was dissolved in a mixture of DMF (90 ml) and DMF.DMA (150 ml) and the mixture was heated under reflux, under an atmosphere of nitrogen, for 18 hours. The reaction mixture was allowed to cool to ambient temperature and the product crystallised. The solid product was collected by filtration, washed with DMF.DMA and then ether and dried under vacuum at 40° C. to give the title compound (11 g, 53%) as a pale solid. NMR: 1.43 (d, 6H), 2.95 (m, 6H), 5.32 (m, 1H), 5.58 (d, 1H), 7.60 (m, 2H), 7.90 (s, 1H).

Method 5

4-(1 -Isopropylimidazol-5-yl)-2-anilinopyrimidine

N-Phenylguanidinium carbonate (15.0 g, 127 mmol) was added to a solution of 5-(3-dimethylaminoprop-2-en-1-oyl)-1-isopropylimidazole (Method 4; 10.5 g, 50.7 mmol) in DMA (250 ml) and the reaction was heated with stirring at 130° C. under nitrogen for 18 hours. The solvent was removed by evaporation, and the residue was partitioned between water and EtOAc. The organic layer was separated and the aqueous layer extracted with EtOAc. The organic extracts were combined, dried and the solvent removed by evaporation. The residue purified by chromatography eluting with DCM/MeOH (97:3) to give the title compound (9.42 g, 67%) as a pale yellow foam. NMR: 1.21 (d, 6H), 5.65 (m, 1H), 6.96 (t, 1H), 7.12 (d, 1H), 7.29 (t, 2H), 7.63 (m, 3H), 8.04 (s, 1H), 8.38 (d, 1H), 9.40 (s, 1H); m/z 280.

Method 6

N-Methoxy-N-methyl 2-thiophenecarboxamide

Thiophen-2-yl carboxyl chloride (7.33 g, 50.0 mmol) was added dropwise to a stirred suspension of N,O-dimethylhydroxylamine hydrochloride (4.87 g, 50.0 mmol) and triethylamine (10.1 g, 100 mmol) in DCM (100 ml) cooled in an ice bath such that the reaction temperature was maintained below 20° C. The mixture was then stirred at ambient temperature for 18 hours. The volatiles were removed by evaporation, and the residue was diluted with water (50 ml) and extracted with EtOAc (2×100 ml). The organic extracts were combined, washed with brine (100 ml), dried and the solvent removed by evaporation to give the title compound (7.56 g, 88%) as a pale brown oil. NMR (CDCl$_3$): 3.66 (s, 3H), 3.78 (s, 3H), 7.10 (dd, 1H), 7.54 (d, 1H), 7.97 (d, 1H); m/z 172.

Method 7

N-Methoxy-N-methyl 4-pyridinecarboxamide

The title compound was generated by the method of Method 6. NMR (CDCl$_3$): 3.37 (s, 3H), 3.54 (s, 3H), 7.51 (d, 2H), 8.71 (d, 2H); m/z 167.

Method 8

N-Methoxy-N-methyl 3-phenylpropionamide

The title compound was generated by the method of Method 6. NMR (CDCl$_3$): 2.75 (t, 2H), 2.95 (t, 2H), 3.18 (s, 3H), 3.60 (s, 3H), 7.14-7.34 (m, 5 H); m/z 194.

Example 10

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% v/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)-(c) may be enteric coated by conventional means, for example to provide a coating of cellulose acetate phthalate.

The invention claimed is:
1. A compound of formula (I):

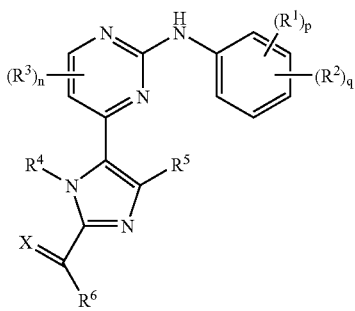

wherein:
R$^1$ is halo, nitro, cyano, hydroxy, amino, carboxy, carbamoyl, mercapto, C$_{1-6}$alkyl, C$_{1-6}$alkoxy, C$_{2-6}$alkenyl or C$_{2-6}$alkynyl;

p is 0-4; wherein the values of R$^1$ may be the same or different;

R$^2$ is sulphamoyl or a group R$^a$-R$^b$-;

q is 0-2; wherein the values of R$^2$ maybe the same or different; and wherein p+q=0-5;

R$^3$ is halo, nitro, cyano, hydroxy, trifluoromethyl, trifluoromethoxy, amino, carboxy, carbamoyl, mercapto, sulphamoyl, C$_{1-3}$alkyl, C$_{2-3}$alkenyl, C$_{2-3}$alkynyl, C$_{1-3}$alkoxy, C$_{1-3}$alkanoyl, N-(C$_{1-3}$alkyl)amino, N,N-(C$_{1-3}$alkyl)$_2$amino, C$_{1-3}$alkanoylamino, N-(C$_{1-3}$alkyl)carbamoyl, N,N-(C$_{1-3}$alkyl)$_2$carbamoyl, C$_{1-3}$alkylS(O)$_a$ wherein a is 0 to 2, N-(C$_{1-3}$alkyl)sulphamoyl or N,N-(C$_{1-3}$alkyl)$_2$sulphamoyl; wherein R$^3$ may be optionally substituted on carbon by one or more R$^c$;

n is 0 to 2, wherein the values of R$^3$ may be the same or different;

R$^4$ is hydrogen, C$_{1-6}$alkyl, C$_{2-6}$alkenyl, C$_{2-6}$alkynyl, C$_{3-8}$cycloalkyl, phenyl or a carbon-linked heterocyclic group; wherein R$^4$ may be optionally substituted on carbon by one or more R$^d$; and wherein if said heterocyclic group contains an —NH— moiety that nitrogen may be optionally substituted by a group selected from R$^n$;

R$^5$ is selected from hydrogen, halo, nitro, cyano, hydroxy, trifluoromethoxy, amino, carboxy, carbamoyl, mercapto, sulphamoyl, C$_{1-6}$alkyl, C$_{2-6}$alkenyl, C$_{2-6}$alkynyl, C$_{1-6}$alkoxy, C$_{1-6}$alkanoyl, C$_{1-6}$alkanoyloxy, N-(C$_{1-6}$alkyl)amino, N,N-(C$_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, N-(C$_{1-6}$alkyl)sulphamoyl, N,N-(C$_{1-6}$alkyl)$_2$sulphamoyl, C$_{1-6}$alkylsulphonylamino, C$_{3-8}$cycloalkyl or a 4-7 membered saturated heterocyclic group; wherein R$^5$ and R$^6$ independently of each other may be optionally substituted on carbon by one or more R$^e$; and wherein if said 4-7 membered saturated heterocyclic group contains an —NH— moiety that nitrogen may be optionally substituted by a group selected from R$^f$;

X is =N—OR$^7$ (wherein "=" indicates the double bond depicted in formula (I);

R$^6$ and R$^7$ are independently selected from hydrogen, C$_{1-6}$alkyl, C$_{3-8}$cycloalkyl, phenyl or a heterocyclic group; wherein R$^6$ and R$^7$ may be independently optionally substituted on carbon by one or more R$^q$; and wherein if said heterocyclic group contains an —NH— moiety that nitrogen may be optionally substituted by a group selected from R$^r$;

R$^a$ is selected from C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, a heterocyclic group, phenylC$_{1-6}$alkyl or (heterocyclic group)C$_{1-6}$alkyl; wherein R$^a$ may be optionally substituted on carbon by one or more R$^g$; and wherein if said heterocyclic group contains an —NH— moiety that nitrogen may be optionally substituted by a group selected from R$^h$;

R$^b$ is —C(O)—, —N(R$^m$)C(O)—, —C(O)N(R$^m$)—, —S(O)$_r$—, —OC(O)N(R$^m$)SO$_2$—, —SO$_2$N(R$^m$)—or —N(R$^m$)SO$_2$—; wherein R$^m$ is hydrogen or C$_{1-6}$alkyl optionally substituted by one or more R$^i$ and r is 1-2;

R$^d$, R$^g$, R$^i$ and R$^q$ are independently selected from halo, nitro, cyano, hydroxy, amino, carboxy, carbamoyl, mercapto, sulphamoyl, C$_{1-6}$alkyl, C$_{2-6}$alkenyl, C$_{2-6}$alkynyl, C$_{2-6}$alkoxy, C$_{1-6}$alkoxy, C$_{1-6}$alkoxyC$_{1-6}$alkoxy, C$_{1-6}$alkoxyC$_{1-6}$alkoxyC$_{1-6}$alkoxy, C$_{1-6}$alkanoyl, C$_{1-6}$alkanoyloxy, N-(C$_{1-6}$alkyl)amino, N,N-(C$_{1-6}$alkyl)$_2$amino, C$_{1-6}$alkanoylamino, N-(C$_{1-6}$alkyl)carbamoyl, N,N-(C$_{1-6}$alkyl)$_2$carbamoyl, C$_{1-6}$alkylS(O)$_a$ wherein a is 0 to 2, C$_{1-6}$alkoxycarbonyl, N-(C$_{1-6}$alkyl)sulphamoyl, N,N-(C$_{1-6}$alkyl)$_2$sulphamoyl, C$_{1-6}$alkylsulphonylamino, C$_{3-8}$cycloalkyl, phenyl, heterocyclic group, phenylC$_{1-6}$alkyl-R$^o$—, (heterocyclic group)C$_{1-6}$alkyl-R$^o$—, phenyl-R$^o$— or (heterocyclic group)-R$^o$—; wherein R$^d$, R$^g$, R$^i$ and R$^q$ independently of each other may be optionally substituted on carbon by one or more R$^j$; and wherein if said heterocyclic group contains an —NH— moiety that nitrogen may be optionally substituted by a group selected from R$^k$;

R$^o$ is —O—, —N(R$^p$)—, —C(O)—, —N(R$^p$)C(O)—, —C(O)N(R$^p$)—, —S(O)$_s$—, —SO$_2$N(R$^p$)— or —N(R$^p$)SO$_2$—; wherein R$^p$ is hydrogen or C$_{1-6}$alkyl and s is 0-2;

R$^f$, R$^h$, R$^k$, R$^n$ and R$^r$ are independently selected from C$_{1-4}$alkyl, C$_{1-4}$alkanoyl, C$_{1-4}$alkylsulphonyl, C$_{1-4}$alkoxycarbonyl, carbamoyl, N-(C$_{1-4}$alkyl)carbamoyl, N,N-(C$_{1-4}$alkyl)carbamoyl, benzyl, benzyloxycarbonyl, benzoyl and phenylsulphonyl; wherein R$^f$, R$^h$, R$^k$, R$^n$ and R$^r$ independently of each other may be optionally substituted on carbon by on or more R$^l$; and R$^c$, R$^e$, R$^j$ and R$^l$ are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl;

or a pharmaceutically acceptable salt thereof.

2. The compound of formula (I) according to claim 1 wherein R$^1$ is halo or a pharmaceutically acceptable salt thereof.

3. The compound of formula (I) according to claim 1 wherein p is 0 or a pharmaceutically acceptable salt thereof.

4. The compound of formula (I) according to claim 1 wherein $R^2$ is a group $R^a$-$R^b$-; wherein
$R^a$ is selected from $C_{1-6}$alkyl; wherein $R^a$ may be optionally substituted on carbon by one or more $R^g$;
$R^b$ is —N($R^m$)SO$_2$—; wherein $R^m$ is hydrogen; and
$R^g$ is $C_{1-6}$alkoxy;
or a pharmaceutically acceptable salt thereof.

5. A compound of formula (I) according to claim 1 wherein q is 0 or 1 or a pharmaceutically acceptable salt thereof.

6. A compound of formula (I) according to claim 1 wherein $R^3$ is halo or a pharmaceutically acceptable salt thereof.

7. A compound of formula (I) according to claim 1 wherein n is 0 or a pharmaceutically acceptable salt thereof.

8. A compound of formula (I) according to claim 1 wherein $R^4$ is $C_{1-6}$alkyl or a pharmaceutically acceptable salt thereof.

9. A compound of formula (I) according to claim 1 wherein X is =N—O$R^7$; wherein $R^7$ is selected from hydrogen or $C_{1-6}$alkyl; wherein $R^7$ may be optionally substituted on carbon by one or more $R^q$; wherein $R^q$ is phenyl; or a pharmaceutically acceptable salt thereof.

10. A compound of formula (I) according to claim 1 wherein $R^6$ is selected from hydrogen, $C_{1-6}$alkyl, phenyl or a heterocyclic group; wherein $R^6$ may be optionally substituted on carbon by one or more $R^q$; and $R^q$ is selected from phenyl.

11. A compound of formula (I) according to claim 1 wherein:
p is 0;
$R^2$ is N-(2-methoxyethyl)sulphamoyl;
q is 0 or 1;
n is 0;
$R^4$ is isopropyl;
$R^5$ is hydrogen;
X is =N—O$R^7$;
$R^6$ is selected from hydrogen, phenyl, pyrid4-yl, thien-2-yl or phenethyl; and
$R^7$ is selected from hydrogen, t-butyl or benzyl;
or a pharmaceutically acceptable salt thereof.

12. A process for preparing a compound of formula (I), as claimed in claim 1, or a pharmaceutically acceptable salt thereof which process (wherein $R^1$, $R^2$, $R^3$, $R^4$, $R^5$, $R^6$, n, p and q are, unless otherwise specified, as defined in claim 1) comprises of:

Process a) reaction of a pyrimidine of formula (II):

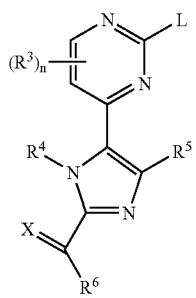

(II)

wherein L is a displaceable group; with an aniline of formula (III):

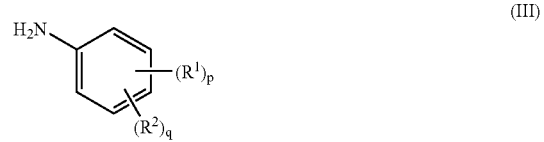

(III)

or

Process b) reacting a compound of formula (IV):

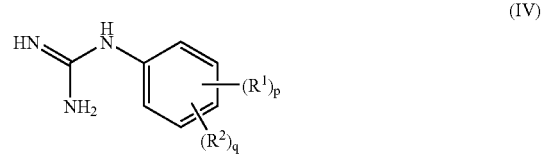

(IV)

with a compound of formula (V):

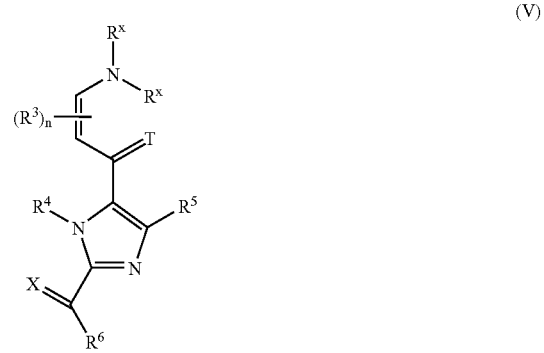

(V)

wherein T is O or S; $R^x$ may be the same or different and is selected from $C_{1-6}$alkyl;

Process c) for compounds of formula (I) where $R^2$ is sulphamoyl or a group $R^a$-$R^b$- and $R^b$ is —NHSO$_2$—; reacting a pyrimidine of formula (VI):

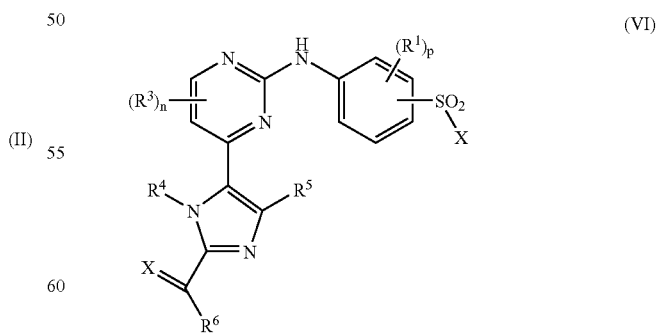

(VI)

wherein X is a displaceable group; with ammonia an amine of formula (VII):

(VII)

Process d) for compounds of formula (I); reacting a pyrimidine of formula (VIII)

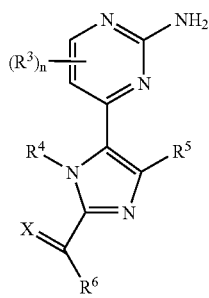
(VIII)

with a compound of formula (IX):

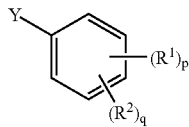
(IX)

where Y is a displaceable group;

Process e) the reaction of a compound of formula (I) wherein X is =O with a compound of formula (X):

$$H_2N-OR^7 \quad (X)$$

and thereafter if necessary:

i) converting a compound of the formula (I) into another compound of the formula (I);
ii) removing any protecting groups;
iii) forming a pharmaceutically acceptable salt thereof.

13. A pharmaceutical composition which comprises a compound of the formula (I), or a pharmaceutically acceptable salt thereof, according to any one of claims 1-11, in association with a pharmaceutically-acceptable diluent or carrier.

14. A method for the treatment of a disease condition selected from breast cancer and rheumatoid arthritis, said method comprising administering to a warm-blooded animal in need thereof a compound of the formula (I), or a pharmaceutically acceptable salt thereof, according to claim 1.

* * * * *